United States Patent [19]
Ulrich et al.

[11] Patent Number: 5,254,098
[45] Date of Patent: Oct. 19, 1993

[54] SUCTION CATHETER ASSEMBLIES

[75] Inventors: Karl Ulrich, Belmont; Tom Devlin, Cambridge, both of Mass.

[73] Assignee: Smiths Industries Medical Systems, Inc., Keene, N.H.

[21] Appl. No.: 18,255

[22] Filed: Feb. 16, 1993

[51] Int. Cl.$^5$ .................................. A61M 16/00
[52] U.S. Cl. ............................ 604/171; 128/207.14; 604/283
[58] Field of Search .......... 604/171, 283, 119, 280; 128/207.16, 207.14

[56] References Cited

U.S. PATENT DOCUMENTS

| | | | |
|---|---|---|---|
| 3,991,762 | 11/1976 | Radford | 604/119 |
| 4,569,344 | 2/1986 | Palmer . | |
| 4,638,539 | 1/1987 | Palmer . | |
| 4,696,296 | 9/1987 | Palmer . | |
| 4,825,859 | 5/1989 | Lambert . | |
| 4,834,726 | 5/1989 | Lambert . | |
| 4,836,199 | 6/1989 | Palmer . | |
| 4,838,255 | 6/1989 | Lambert . | |
| 4,850,350 | 7/1989 | Jackson | 128/207.16 |
| 4,872,579 | 10/1989 | Palmer | 128/207.16 |
| 4,938,741 | 7/1990 | Lambert . | |
| 4,967,743 | 11/1990 | Lambert . | |
| 4,981,466 | 1/1991 | Lambert . | |
| 5,025,806 | 6/1991 | Palmer . | |
| 5,029,580 | 7/1991 | Radford . | |
| 5,060,646 | 10/1991 | Page . | |
| 5,065,755 | 11/1991 | Jensen . | |
| 5,073,164 | 12/1991 | Hollister et al. | 604/43 |
| 5,083,861 | 1/1992 | Russo | 128/207.14 |
| 5,088,486 | 2/1992 | Jinotti | 128/207.14 |
| 5,122,123 | 6/1992 | Vaillancourt | 604/283 |
| 5,125,893 | 6/1992 | Dryden | 604/171 |
| 5,125,915 | 6/1992 | Berry et al. | 604/283 |
| 5,139,483 | 8/1992 | Ryan | 604/283 |

*Primary Examiner*—Paul J. Hirsch
*Attorney, Agent, or Firm*—Pollock, Vande Sande & Priddy

[57] ABSTRACT

A closed system suction catheter assembly has a catheter that is protected along its length by a flexible sleeve. The catheter extends through a patient connecting member by which the assembly is connected to a tracheal tube. Within the connecting member there is a sliding seal support with a groove in which is located a rib that extends along the outside of the catheter. The rib follows a sinusoidal path so that the catheter is twisted backwards and forwards as the catheter is pushed or pulled through the patient connecting member.

9 Claims, 2 Drawing Sheets

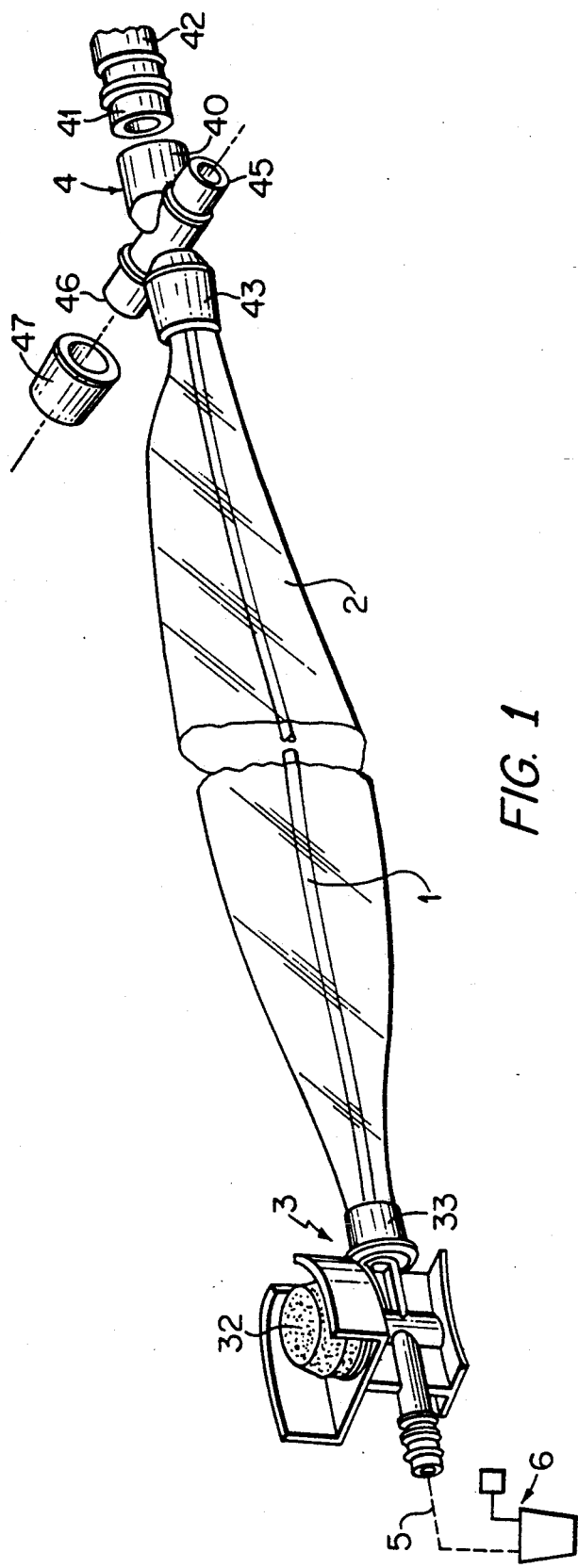
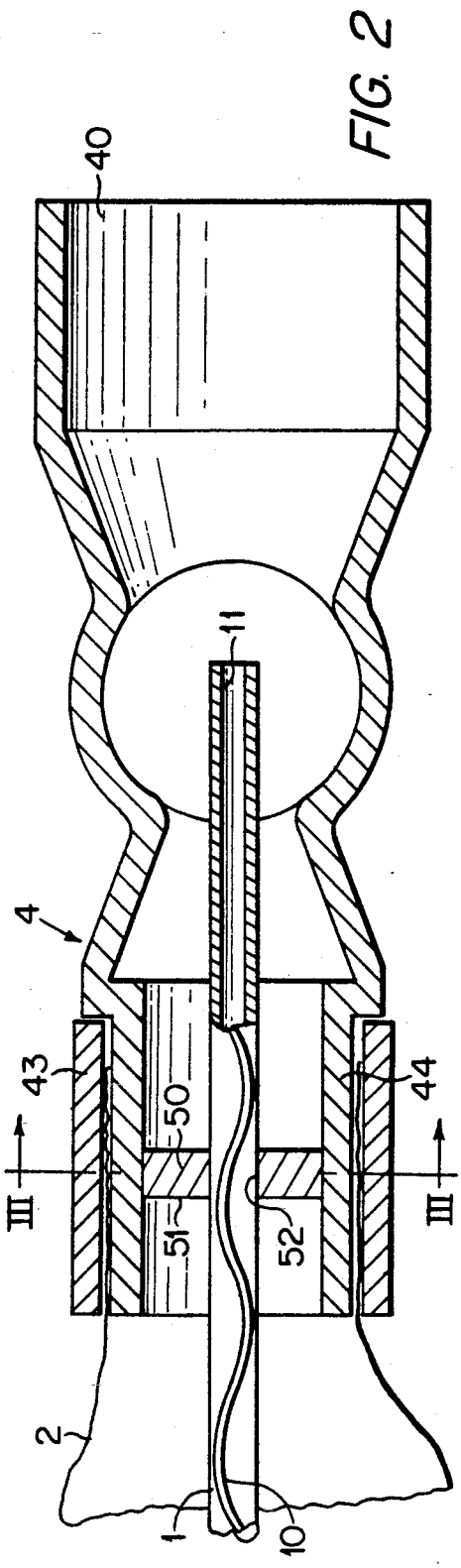
FIG. 1
FIG. 2

SUCTION CATHETER ASSEMBLIES

BACKGROUND OF THE INVENTION

This invention relates to suction catheter assemblies.

The invention is more particularly concerned with assemblies of the kind having an aspirating catheter enclosed within a protective, flexible sleeve and which can be advanced through a coupling at one end of the assembly. The coupling has one port connected to a tracheal tube and two further side ports by which ventilation of the patient can take place. In use, the machine end of the catheter is connected to a suction source via a valve. Secretions that build up on the inside of the tracheal tube, the trachea and bronchi can be periodically removed by advancing the catheter through the coupling and down the tracheal tube and opening the valve. The coupling enables ventilation of the patient to continue while suctioning takes place.

Examples of catheter assemblies having an aspirating catheter which is contained within a sleeve and which can be pushed through a sliding seal on coupling are described in several patents, such as U.S. Pat. No. 3,991,762 to Radford; U.S. Pat. No. 4,569,344 to Palmer; U.S. Pat. No. 4,638,539 to Palmer; U.S. Pat. No. 4,696,296 to Palmer; U.S. Pat. No. 4,825,859 to Lambert; U.S. Pat. No. 4,834,726 to Lambert; U.S. Pat. No. 4,836,199 to Palmer; U.S. Pat. No. 4,838,255 to Lambert; U.S. Pat. No. 4,872,579 to Palmer; U.S. Pat. No. 4,938,741 to Lambert; U.S. Pat. No. 4,967,743 to Lambert; U.S. Pat. No. 4,981,466 to Lambert; U.S. Pat. No. 5,025,806 to Palmer; U.S. Pat. No. 5,029,580 to Radford; U.S. Pat. No. 5,060,646 to Page; U.S. Pat. No. 5,065,754 to Jensen; U.S. Pat. No. 5,073,164 to Hollister; and GB 2207736 to Hollister. Suction catheter assemblies of this kind are also available from Smiths Industries Medical Systems Inc under the trade mark STERI-CATH and from Ballard Medical Products Inc under the trade mark TRACHCARE.

It is sometimes desired to rotate the catheter as it is advanced and withdrawn from the tracheal tube and trachea so that the aspirating tip of the catheter is wiped around the internal circumference of the tube and trachea. In this way, a maximum amount of the secretions can be removed. It has been proposed in U.S. Pat. No. 3,991,752 to provide the catheter with a wheel by which the catheter can be rotated. This, however, has the disadvantage in that it requires the clinician to twist the wheel at the same time as advancing the catheter which can be a difficult manoeuvre to perform.

BRIEF SUMMARY OF THE INVENTION

It is an object of the present invention to provide a suction catheter assembly which can be used more easily.

According to one aspect of the present invention there is provided a suction catheter assembly for use in removing fluid from a patient, the assembly comprising: an aspirating catheter having a proximal and distal end, said distal end being suitable for insertion into a patient; a vacuum connecting member located in the vicinity of the proximal end of the catheter; a patient connecting member mounted to surround the catheter in the vicinity of the distal end of the catheter; a protective sleeve extending along the aspirating catheter where it extends between the patient connecting member and the vacuum connecting member; and a linear-to-angular motion coupling between the catheter and the patient connecting member such that linear displacement of the catheter through the patient connecting member automatically effects angular displacement of the catheter.

The linear-to-angular motion coupling may be provided by a projecting rib on the catheter that describes a sinusoidal path and a groove on a support in which the rib locates. The linear-to-angular motion coupling preferably provides a sliding seal between the catheter and the patient connecting member. Alternatively, the linear-to-angular motion coupling may be provided by a circular member and an external sleeve within which the circular member is mounted, the circular member having an aperture through which the catheter extends said aperture being located offset from the centre of the circular member, and the circular member and the sleeve having cooperating surface formations which enable limited linear displacement of the circular member and convert said linear displacement to angular displacement of the circular member. The circular member preferably has a groove around its circumference, the external sleeve having at least one projection that engages in the groove. The aperture in the circular member may make a sliding seal with the catheter.

According to another aspect of the present invention there is provided a suction catheter assembly for use in removing fluid from a patient, the assembly comprising: an aspirating catheter having a proximal and distal end, said distal end being suitable for insertion into a patient; a sinusoidal rib extending along the length of the catheter; a vacuum connecting member located in the vicinity of the proximal end of the catheter; a patient connecting member mounted to surround the catheter in the vicinity of the distal end of the catheter; a protective sleeve extending along the aspirating catheter where it extends between the patient connecting member and the vacuum connecting member; and a support, said support forming a sliding seal with the catheter and support having a groove in which the rib of the catheter is located such that insertion of the catheter through the support causes the catheter to twist backwards and forwards.

According to a further aspect of the present invention there is provided a suction catheter assembly for use in removing fluid from a patient, the assembly comprising: an aspirating catheter having a proximal and distal end, said distal end being suitable for insertion into a patient; a vacuum connecting member located in the vicinity of the proximal end of the catheter; a patient connecting member mounted to surround the catheter in the vicinity of the distal end of the catheter; a protective sleeve extending along the aspirating catheter where it extends between the patient connecting member and the vacuum connecting member; and a rotatable piston, said piston being located in the patient connecting member and having an aperture offset from the centre of the piston which forms a sliding seal with the catheter, and the piston having a sinusoidal groove around its circumference, the patient connecting member having a projection, said projection engaging in the groove around the piston such that when the catheter is pushed and pulled through the patient connecting member it causes the piston and the catheter to twist.

A suction catheter assembly according to the present invention, will now be described, by way of example, with reference to the accompanying drawings.

BRIEF DESCRIPTION OF THE DRAWINGS

FIG. 1 is a perspective view of the assembly;

FIG. 2 is an enlarged sectional side elevation of a part of the assembly;

DESCRIPTION OF THE PREFERRED EMBODIMENTS

Figure 3:
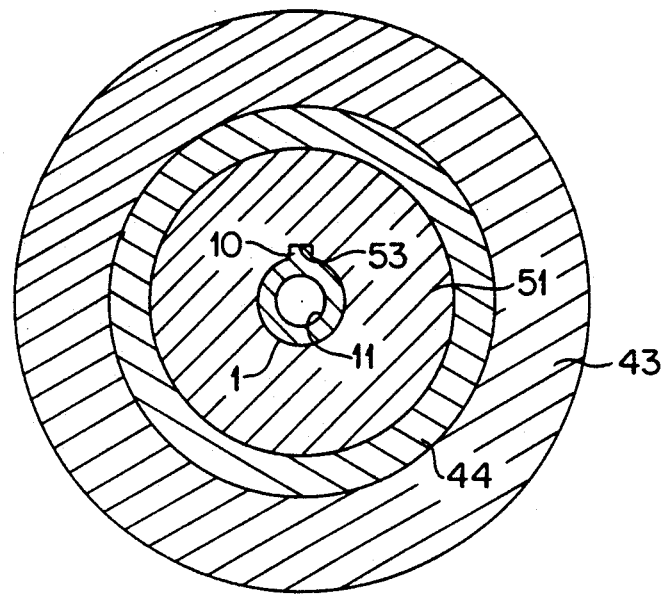
FIG. 3 is a transverse section along the line III—III of FIG. 2.

The suction catheter assembly comprises an aspirating catheter 1 that extends within a flexible, protective sleeve 2 between a vacuum connecting member 3 and a patient connecting member 4.

The aspirating catheter 1 has an outside diameter of about 4-5 mm and a length of about 55 cm. The catheter 1 has a projecting rib 10 which extends along the external surface of the catheter and which describes a sinusoidal path. Typically, the height and width of the rib 10 is about 1.5 mm wide and the path it describes has a pitch of about 25 mm extending in a strip along the catheter which occupies about 120° about its circumference. In the illustrated example, the catheter 1 has a single lumen 11 although catheters with multiple lumens for use in irrigation, oxygen supply or medication delivery could be used. At its machine or proximal end, the catheter 1 is secured to the vacuum connecting member 3.

The vacuum connecting member 3 is moulded from a rigid plastics material and has a bore (not shown) extending along, it into one end of which the catheter 1 is bonded. The opposite end of the bore extends through a spigot 31 which, in use, is connected to tubing 5 which extends to a vacuum or suction source 6. The vacuum connecting member 3 includes a conventional manually-operated valve 32 which normally prevents flow through the connecting member 3 and catheter 1 but which can be pressed down by the user to open the valve and connect the lumen 11 of the catheter to the suction source 6.

The proximal end of the sleeve 2 is secured to the vacuum connecting member 3 beneath a collar 33 secured to the distal end of the vacuum connecting member. The distal end of the sleeve 2 is similarly secured to the patient connecting member 4 by means of a collar 43 on a proximal extension 44 of the patient connecting member.

The patient connecting member 4 is of generally cruciform shape. At its distal, or patient end, the connecting member 4 has a female luer coupling 40 which is aligned with the axis of the member and with the proximal extension 44. The coupling 40 is adapted to be connected to a cooperating coupling 41 on the end of a tracheal tube 42. Two side ports 45 and 46 extend at right angles to the axis of the connecting member, directly opposite one another, about midway along the length of the connecting member. These two side ports 45 and 46 communicate directly with the interior of the coupling 40 and are used in the conventional manner to connect with ventilation apparatus. One port may be used for inhalation gas and the other port used for exhalation gas. Alternatively, one of the ports 46 may be closed by a cap 47 and inhalation and exhalation both be effected through the other port 45.

The patient connecting member 4 includes a catheter support 50 which serves dual functions as a seal and as a linear-to-angular motion coupling. The support 50 is in the form of an annular collar 51 of circular shape made of a resilient but relatively hard plastics material with a low coefficient of friction, such as nylon. The collar 51 has a circular aperture 52, with a diameter equal to the external diameter of the catheter 1, and a groove 53 which is a close fit about the rib 10 on the catheter. It is not essential that the support 50 also serves as a seal since a separate seal could be used.

In operation, the coupling 40 of the connecting member 4 is secured to the coupling 41 on the end of the tracheal tube 42, and its side ports 45 and 46 are connected to a ventilator. The vacuum coupling member 3 is connected to the suction source 6 but, as long as the manual valve 32 remains unactuated, no suction is applied to the catheter 1.

When aspiration of fluid from the trachea or bronchi is required, the user grips the catheter 1 through the sleeve 2 and pushes it forwardly so that the distal, patient end of the catheter is advanced through the connecting member 4 and into the tracheal tube 42. As the catheter 1 is advanced through the patient connecting member 4, the rib 10 on the catheter will slide through the groove 53 in the collar 51 and the catheter will, therefore, be automatically angularly displaced in an oscillating, backwards and forwards twisting fashion. This causes the tip of the catheter 1 to wipe around the inside of the tracheal tube 42 as the catheter is pushed in. Even though the catheter 1 is only twisted through about 120° at the support 50, the flexibility of the catheter and the distance between the tip and the support means that the swing will be amplified at the tip and that the major part of the circumference of the tube 42 will be swept by the tip. When the catheter 1 has been inserted to the desired depth, the user depresses the valve 32 so that the catheter is connected to the suction source 6 and fluid in the vicinity of the tip of the catheter is sucked into the catheter and removed. The catheter 1 is then pulled back while the valve is held open so that the action of withdrawing the catheter through the support causes the tip to swing around the inside of the tracheal tube. During aspiration, ventilation of the patient occurs normally. The assembly remains attached to the tracheal tube connector so that it can be reused when necessary.

Instead of a projecting rib, the catheter could have a groove extending along its outside surface which describes the same sinusoidal path as the rib. In this embodiment, the collar of the support would have a projecting lug that lies in the groove of the catheter. Alternatively, the catheter could have a non-circular section, such as, for example, an oval shape which is twisted along its length, the support having an oval aperture so that, as the catheter is displaced linearly, the support displaces it angularly.

Figure 4:
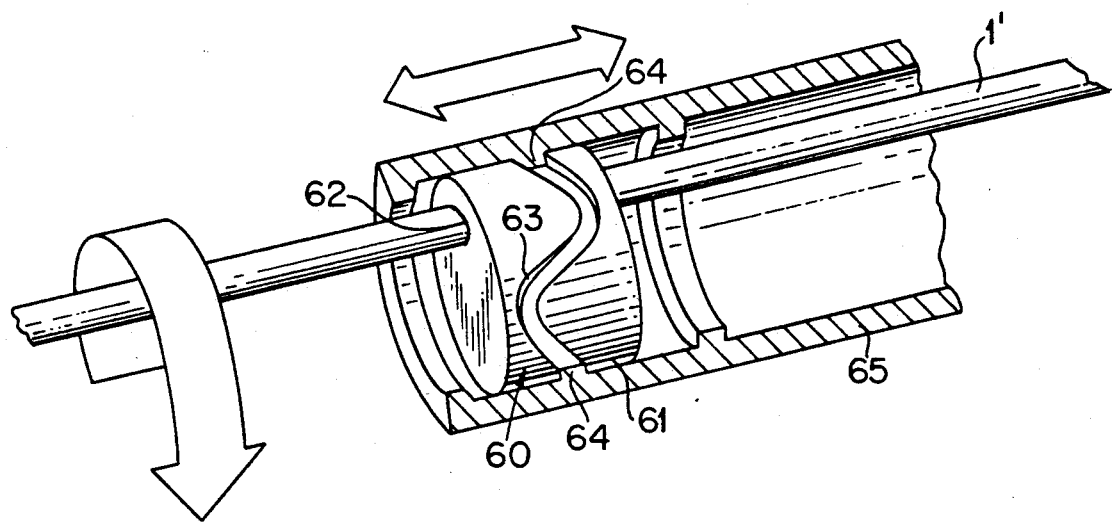
FIG. 4 is a cut-away perspective view of a part of an alternative assembly.

Various other arrangements are possible in which the catheter has an uninterrupted smooth surface. One example is shown in FIG. 4 in which the assembly has a linear-to-angular motion coupling 60 including a rotatable circular member or piston 61. The piston 61 has an off-centre aperture 62 which forms a sliding seal with the catheter 1'. Around the circumference of the piston 61 there is a sinusoidal groove 63 in which locate two diammetrically opposite lugs 64 that project from the inside of an external sleeve 65 formed by a part of the patient connecting member 4. The piston 61 is a close fit within the sleeve 65 but can be easily rotated and displaced axially for a limited distance, as constrained by engagement of the lugs 64 in the groove 63 which provide cooperating surface formations.

With this arrangment, the clinician advances the catheter 1' by repeatedly pushing and pulling it through the patient connecting member. The friction of the catheter 1' in the aperture 62 causes the piston 61 to be displaced forwardly and rearwardly by this movement of the catheter and hence converts the linear displacement of the piston to angular displacement and causes the piston to twist. This in turn causes the catheter also to twist.

What we claim is:

1. A suction catheter assembly for use in removing fluid from a patient, the assembly comprising: an aspirating catheter having a proximal and distal end, said distal end being suitable for insertion into a patient; a vacuum connecting member located in the vicinity of the proximal end of the catheter; a patient connecting member mounted to surround the catheter in the vicinity of the distal end of the catheter; a protective sleeve extending along the aspirating catheter where it extends between the patient connecting member and the vacuum connecting member; and a linear-to-angular motion coupling between the catheter and the patient connecting member such that linear displacement of the catheter through the patient connecting member automatically effects angular displacement of the catheter.

2. A suction catheter assembly according to claim 1, wherein the linear-to-angular motion coupling is provided by a projecting rib on the catheter that describes a sinusoidal path and a groove on a support in which the rib locates.

3. A suction catheter assembly according to claim 1, wherein the linear-to-angular motion coupling provides a sliding seal between the catheter and the patient connecting member.

4. A suction catheter assembly according to claim 1, wherein the linear-to-angular motion coupling is provided by a circular member and an external sleeve within which the circular member is mounted, wherein the circular member has an aperture through which the catheter extends said aperture being located offset from the centre of the circular member, and wherein the circular member and the sleeve have cooperating surface formations which enable limited linear displacement of the circular member and convert said linear displacement to angular displacement of the circular member.

5. A suction catheter assembly according to claim 4, wherein the circular member has a groove around its circumference, and wherein the external sleeve has at least one projection that engages in the groove.

6. A suction catheter assembly according to claim 4, wherein the aperture in the circular member makes a sliding seal with the catheter.

7. A suction catheter assembly according to claim 2, wherein the linear-to-angular motion coupling provides a sliding seal between the catheter and the patient connecting member.

8. A suction catheter assembly for use in removing fluid from a patient, the assembly comprising: an aspirating catheter having a proximal and distal end, said distal end being suitable for insertion into a patient; a sinusoidal rib extending along the length of the catheter; a vacuum connecting member located in the vicinity of the proximal end of the catheter; a patient connecting member mounted to surround the catheter in the vicinity of the distal end of the catheter; a protective sleeve extending along the aspirating catheter where it extends between the patient connecting member and the vacuum connecting member; and a support, said support forming a sliding seal with the catheter and support having a groove in which the rib of the catheter is located such that insertion of the catheter through the support causes the catheter to twist backwards and forwards.

9. A suction catheter assembly for use in removing fluid from a patient, the assembly comprising: an aspirating catheter having a proximal and distal end, said distal end being suitable for insertion into a patient; a vacuum connecting member located in the vicinity of the proximal end of the catheter; a patient connecting member mounted to surround the catheter in the vicinity of the distal end of the catheter; a protective sleeve extending along the aspirating catheter where it extends between the patient connecting member and the vacuum connecting member; and a rotatable piston, said piston being located in the patient connecting member and having an aperture offset from the centre of the piston which forms a sliding seal with the catheter, said piston having a sinusoidal groove around its circumference, and wherein the patient connecting member has a projection, said projection engaging in the groove around the piston such that when the catheter is pushed and pulled through the patient connecting member it causes the piston and the catheter to twist.

* * * * *